United States Patent
Scheltienne et al.

(10) Patent No.: US 11,491,336 B2
(45) Date of Patent: Nov. 8, 2022

(54) NEUROMODULATION SYSTEM

(71) Applicant: ONWARD MEDICAL N.V., Eindhoven (NL)

(72) Inventors: Mathieu Scheltienne, Eindhoven (NL); Jeroen Tol, Eindhoven (NL); Robin Brouns, Eindhoven (NL)

(73) Assignee: ONWARD MEDICAL N.V., Eindhoven (NL)

( * ) Notice: Subject to any disclaimer, the term of this patent is extended or adjusted under 35 U.S.C. 154(b) by 51 days.

(21) Appl. No.: 17/105,345

(22) Filed: Nov. 25, 2020

(65) Prior Publication Data

US 2021/0154481 A1 May 27, 2021

(30) Foreign Application Priority Data

Nov. 27, 2019 (EP) ..................................... 19211738

(51) Int. Cl.
*A61N 1/36* (2006.01)

(52) U.S. Cl.
CPC ..... *A61N 1/36192* (2013.01); *A61N 1/36067* (2013.01); *A61N 1/36142* (2013.01); *A61N 1/36175* (2013.01); *A61N 1/36178* (2013.01); *A61N 1/36196* (2013.01)

(58) Field of Classification Search
CPC .............. A61N 1/3603; A61N 1/36067; A61N 1/36128; A61N 1/36142; A61N 1/36175; A61N 1/36178; A61N 1/36192; A61N 1/36196; A61N 1/37235; A61N 1/37247; G16H 20/30; G16H 40/63
See application file for complete search history.

(56) References Cited

U.S. PATENT DOCUMENTS

| | | | |
|---|---|---|---|
| 8,108,051 B2 | 1/2012 | Cross, Jr. et al. | |
| 2012/0006793 A1 | 1/2012 | Swanson | |
| 2013/0096662 A1 | 4/2013 | Swanson | |

FOREIGN PATENT DOCUMENTS

| | | | | |
|---|---|---|---|---|
| EP | 0630987 A1 | 12/1994 | | |
| EP | 3323468 A1 | * 5/2018 | ............. | A61N 1/025 |
| WO | 2014209877 A1 | 12/2014 | | |
| WO | 2016172239 A1 | 10/2016 | | |
| WO | 2017117450 A1 | 7/2017 | | |

OTHER PUBLICATIONS

European Search Report and Opinion for EP 19211738, dated May 27, 2020, Retrieved Mar. 12, 2021 (Year: 2020).*

* cited by examiner

*Primary Examiner* — Amanda K Hulbert
(74) *Attorney, Agent, or Firm* — Finnegan, Henderson, Farabow, Garrett & Dunner, LLP

(57) ABSTRACT

A neuromodulation system including at least one input module for inputting a planned neuromodulation event or a series of neuromodulation events and at least one analyzing module for analyzing a neuromodulation event or a series of neuromodulation events.

The analyzing module and the input module may be connected such that the input module is configured to forward the planned neuromodulation event or a series of neuromodulation events to the analyzing module and the analyzing module is configured to analyze the planned neuromodulation event or a series of neuromodulation events regarding one or more possible neuromodulation conflict(s).

20 Claims, 12 Drawing Sheets

FIG. 8

NEUROMODULATION SYSTEM

CROSS-REFERENCE TO RELATED APPLICATION

The present application claims priority to EP 19211738.0 entitled "Neuromodulation system" and filed Nov. 27, 2019. The entire contents of the above-referenced application is hereby incorporated by reference for all purposes.

TECHNICAL FIELD

The present invention relates to neuromodulation systems, and more particularly, to a system for planning and/or controlling a neuromodulation system.

BACKGROUND

Neuromodulation, in particular neurostimulation, in particular electrical neurostimulation, may be applied to a subject by a neuromodulation system comprising at least one electrode array comprising at least one electrode. Neuromodulation systems may further comprise at least one of a controller, e.g. a microcontroller, a processor, e.g. a microprocessor, a pulse generator, in particular an implantable pulse generator, a sensor, a communication module, and a telemetry module.

The electrode array, e.g. comprised in a lead paddle, can be applied for percutaneous electrical stimulation, transcutaneous electrical nerve stimulation (TENS), epidural electrical stimulation (EES), subdural electrical stimulation (SES), functional electrical stimulation (FES) and/or all neurostimulation and/or muscle stimulation applications that use at least one electrode array and/or at least one electrode. Lead paddles are for example described by U.S. Pat. No. 8,108,051B2, US 2013/0096662 A1, US 2012/0006793 A1 and EP3013411A1.

Neurostimulation, in particular multi-channel and/or variable neurostimulation, often requires an interface to create the stimulation program and a stimulation system to deliver the stimulation. WO2017117450A1 generally describes a system for programming a neurostimulator including a storage device and a pattern generator. The storage device may store a pattern library and one or more neuronal network models. The pattern library may include fields and waveforms of neuromodulation. The one or more neuronal network models may each be configured to allow for evaluating effects of one or more fields in combination with one or more waveforms in treating one or more indications for neuromodulation. The pattern generator may be configured to construct and approximately optimize a spatio-temporal pattern of neurostimulation and/or its building blocks for a specified range of varying conditions using at least one neuronal network model.

EP 3 285 855 B1 generally describes a system for delivering neurostimulation including a programming control circuit and a user interface. The programming control circuit may be configured to generate stimulation parameters controlling delivery of neurostimulation pulses according to one or more stimulation waveforms associated with areas of stimulation each defined by a set of electrodes. The neurostimulation pulses are each delivered to an area of stimulation. The user interface may include a display screen and an interface control circuit. The interface control circuit may be configured to define the one or more stimulation waveforms and the areas of stimulation and may include a stimulation frequency module configured to display a stimulation rate table on the display screen. The stimulation rate table may present stimulation frequencies associated with each of the areas of stimulation for selection by a user.

EP630987 B1 generally describes an external control device for use with a neurostimulation system having a neurostimulation lead and a plurality of electrodes circumferentially disposed around the neurostimulation lead capable of conveying an electrical stimulation field into tissue in which the electrodes are implanted, comprising: a user interface including a display screen configured for displaying three-dimensional graphical renderings of the electrodes a plurality of iconic control elements graphically linked to the graphical renderings of the electrodes and indicating an amount of current through the corresponding electrode in terms of a fractionalized current value for a displayed set of stimulation parameters, and a first circumferential modification control element and a second circumferential modification control element configured for being actuated; a processor configured for generating stimulation parameters designed to modify the electrical stimulation field when the first circumferential modification control element is actuated to circumferentially contract the electrical stimulation field about a locus of the electrical stimulation field and when the second circumferential modification control element is actuated to circumferentially expand the electrical stimulation field about the locus of the electrical stimulation field; and output circuitry configured for transmitting the stimulation parameters to the neurostimulation system.

However, the user's input, i.e. the stimulation program, may not necessarily match the nature and capacity of the electrode array, resulting in a conflict in terms of feasibility of the stimulation program.

SUMMARY

Provided is a neuromodulation system which allows finely tuned neuromodulation with regard to the feasibility of the planned stimulation program. The neuromodulation system may include one or more components or modules including, but not limited to, an input module for inputting a planned neuromodulation event or a series of neuromodulation events, an analyzing module for analyzing a neuromodulation event or a series of neuromodulation events, in which the analyzing module and the input module are connected such that the input module is configured to forward the planned neuromodulation event or a series of neuromodulation events to the analyzing module and the analyzing module is configured to analyze the planned neuromodulation event or a series of neuromodulation events regarding one or more possible neuromodulation conflict(s).

While the neuromodulation system may be used for any purpose, in some aspects, the neuromodulation system may be used for restoring autonomic function and/or motoric function. In some embodiments, the neuromodulation system may also be used in a decoupled manner to set a neuromodulation system based on patient data and/or feedback information, e.g. as a generic system decoupled from an implanted neuromodulation system. In some embodiments, the neuromodulation system may be a neurostimulation system.

In some aspects, the neuromodulation system may be used for percutaneous electrical stimulation, TENS, EES, SES, FES and/or all neurostimulation and/or muscle stimulation applications that use at least one electrode array and/or at least one electrode. The neuromodulation system may be a closed-loop system or an open-loop system.

The neuromodulation system may be used in a method for the treatment of motor impairment and/or restoring motor function. Motor function may comprise all voluntary postures and movement patterns, such as locomotion. In additional aspects, the neuromodulation system may be used in a method for the treatment of autonomic dysfunction and/or restoring autonomic function. Autonomic dysfunction may comprise altered and/or impaired regulation of at least one of blood pressure, heart rate, thermoregulation (body temperature), respiratory rate, immune system, gastro-intestinal tract (e.g. bowel function), metabolism, electrolyte balance, production of body fluids (e.g. saliva and/or sweat), pupillary response, bladder function, sphincter function and sexual function. In further aspects, the neuromodulation system may be used in a method for the treatment of autonomic dysreflexia, spasticity, altered and/or impaired sleep behavior and/or pain.

A neuromodulation event may be or may comprise start, stop, up ramping, down ramping, duration, repetition and/or cycles of stimulation of at least one muscle and/or stimulation block. A series of neuromodulation events can also be referred to as stimulation program and/or stimulation partiture.

By analyzing any potential conflict(s) between a planned neuromodulation event or a series of neuromodulation events and boundary conditions of the planned neuromodulation, e.g. system-related, patient-related, or user made, before the beginning of the neurostimulation, the neurostimulation outcome (e.g. of a patient) closest to the planned neuromodulation event or a series of neuromodulation events and feasible with the boundary conditions and/or any type of preestablished limitation, may be enabled. In some embodiments, the conflicts may be analyzed before the stimulation settings are uploaded to a controller and/or a pulse generator.

A stimulation block determines an electrode configuration and/or stimulation configuration, and/or an amplitude/intensity of stimulation and a pulse train, wherein a pulse train may be defined as a temporal arrangement of stimulation events. During movement, e.g. a gait cycle, different stimulation blocks need to be stimulated consequentially and/or at least partially simultaneously with different pulsed electrical waveforms at different frequencies and amplitudes, sometimes with different pattern of pulses, in order to reproduce a movement, e.g. a gait cycle comparable to a healthy subject. The neurostimulation system may be or may comprise a pulse generator, in some embodiments an implantable pulse generator (IPG) and/or non-implantable pulse generator. The neurostimulation system may comprise a lead and/or an electrode array comprising at least one electrode, preferably multiple electrodes. The neurostimulation system may further comprise a controller, a microcontroller, a processer, a microprocessor, a communication system, a telemetry system, a sensor, a sensor network, a display, and/or a training device. Collectively, the various tangible components or a subset of the tangible components may be referred to herein as "logic" configured or adapted in a particular way, for example as logic configured or adapted with particular software or firmware. In some aspects, logic and memory may be integrated into one or more common devices, such as an application specific integrated circuit, field programmable gate array, or a system on a chip.

The input module may be or may comprise a user interface, in some embodiments a graphical user interface. In some embodiments, the input module may enable verification and optimization of a neuromodulation program (also referred to as stimulation partiture) and/or neuromodulation settings. In some embodiments, a user, e.g. a therapist, physiotherapist, medical doctor, nurse, patient and/or patient relative may input a stimulation program comprising a neuromodulation event or a series of neuromodulation events on the input module.

The input module sends information to an analyzing module. The analyzing module processes the stimulation program to identify conflicts in the planned neuromodulation event or series of neuromodulation events. Such conflicts may be from any source including, but not limited to, neuromodulation safety, hardware capabilities, and/or software capabilities.

The system may further comprise at least one correction module which is configured to amend the planned neuromodulation event or a series of neuromodulation events such that in case of detection of a neurostimulation conflict the neuromodulation event or a series of neuromodulation events is/are amended such that the neuromodulation conflict is avoided. In some embodiments, this may allow correction of the conflict(s) before the beginning of the planned stimulation program, the planned neuromodulation may be made compatible with the system capabilities and the patient. In some embodiments, a neurostimulation outcome may be secured by detecting conflict(s) between a planned stimulation program and a stimulation system to deliver the stimulation and by proposing an appropriate fix to resolve the conflict(s) before the planned neurostimulation program is uploaded on the stimulation system, and thus before the beginning of the planned exercise and/or physiological process. In other words, each time a new neuromodulation event and/or series of neuromodulation event is inputted, this input may be analyzed by the neuromodulation system and corrected before the stimulation is started. This ensures that after transferring the stimulation program to the stimulation system all parameters are verified. Consequently, the stimulation program can be executed by the system and is compatible with the patient.

The analysis by the analyzing module and/or the correction by the correction module may be applied to either a time segment of stimulation, e.g. a neuromodulation event, or to the complete stimulation program, e.g. a series of neuromodulation events, e.g. by looking at a variable over the complete stimulation duration instead of during a single time segment.

The neuromodulation system may further comprise output means, wherein the output means are connected to the analyzing module and which are configured to provide at least partially a visual output of at least one of the analysis performed by the analyzing module, the planned neuromodulation event or a series of neuromodulation events, the neuromodulation conflict(s), the correction of the planned neuromodulation event or a series of neuromodulation events. This may enable that a user, e.g. a physiotherapist, a therapist, a medical doctor, a patient, and/or a patient relative, may watch and/or control the analysis performed by the analyzing module, the planned neuromodulation event or a series of neuromodulation events, the neuromodulation conflict(s), the correction of the planned neuromodulation event or a series of neuromodulation events. In other words, the output means may make the neuromodulation system transparent for the user. In some embodiments, the output means may be a display and/or a touch screen and/or a graphical user interface. For example, the display may be used to present a visual representation of data using, for example, a "graphics processing unit" (GPU), a processing unit that comprises a programmable logic chip (processor) specialized for display functions. The GPU may render images, animations, and video for a computer screen. The GPU may be located on plug-in cards, in a chipset of a motherboard of a computer, or in the same chip as the central processing unit (CPU) of the device. In some aspects, the output means may alternatively be referred to as output module.

The input module, the analyzing module, the correction module and/or the output means may be implemented on a programmer, e.g. a space-time programmer (STP).

The neuromodulation system may be further configured for a semi-automatic or automatic correction of the neuromodulation conflict. In some embodiments, the amendment of the planned neuromodulation event or series of neuromodulation events may be at least partly based on an algorithm provided by the correction module. In some embodiments, semi-automatic correction may be a combination of an algorithm provided by the correction module and an intervention of a user, e.g. through the input module, in some embodiments through a user-interface such as, but not limited to, one or more user input devices, such as a keyboard, mouse, track ball, stylus, touch screen, microphone, natural user interface, etc. connected via wired or wireless connections. Semi-automatic or automatic correction of the neuromodulation conflict may enable correction within a minimum of time, such that the planned neuromodulation may be provided with no or minimum time delay, e.g. in real-time or close to real-time.

Embodiments of the present disclosure provide that there may be also a manual and/or completely manual correction functionality. Such manual correction capability can be provided alternatively or additionally. The manual correction capability can be provided through mechanisms like a tool (or several tools) and/or instructions (like instructions in a user manual) and may be provided via a user interface (e.g. a graphical user interface).

The one or more possible neuromodulation conflict(s) may be related to at least one of neuromodulation safety, hardware capabilities, and/or software capabilities. By analyzing and/or correcting conflict(s) related to neuromodulation safety, hardware capabilities and/or software capabilities, the neuromodulation system enables correction of conflicts of multiple origins, in some embodiments any form of at least partially calculable conflict source is thereby correctable.

The hardware capabilities may include capabilities of the neuromodulation system or its components, e.g. the input module, the analyzing module, the correction module, the output means, at least one of a controller, a microcontroller, a processer, a microprocessor, a communication system, a telemetry system, a sensor, a sensor network, a display, a pulse generator, a lead and/or a training device.

Correcting neuromodulation conflict(s) related to hardware capabilities may enable adequate timing between pulses provided to set the current source/voltage source to the correct value and/or delivering the required current/voltage at any given instant. Correcting neuromodulation conflict(s) related to neuromodulation safety may enable an adequate grounding time, and/or keeping electrical simulation within limited boundaries and/or comfortability. Correcting neuromodulation conflict(s) related to software capabilities may enable that the quantity of information is compatible with the memory capacity available and that, e.g. a microcontroller computational load is compatible with its speed.

The neurostimulation system may comprise a neurostimulation array, wherein the neurostimulation array may be or may comprise an array of multiple electrodes and wherein a neuromodulation conflict may be detected, when the planned neuromodulation event or a series of neuromodulation events may require an impossible electrode configuration.

In some embodiments, more than one stimulation block may be requested to be stimulated at the same time, yet the more than one stimulation block may share electrodes of the array of multiple electrodes. In some embodiments, detecting a neuromodulation conflict may enable merging the electrode configurations of the more than one stimulation block, providing an alternative electrode configuration and/or keeping the electrode configuration as planned but avoiding pulse overlap. In some embodiments this may enable creating a solution, where during the period of conflict a correction of the conflict may be enabled, enabling best possible neuromodulation.

The correction can be applied with or without display of the conflicts on the user interface, and with or without the intervention of the user through the user interface.

In some embodiments, the method may be a method for performing neuromodulation, the method comprising at least the following steps:

analyzing a neuromodulation event or a series of neuromodulation events, wherein the analyzing includes the analysis whether the planned neuromodulation event or a series of neuromodulation events comprises one or more possible neuromodulation conflict(s).

The method may further comprise the step of correcting the neuromodulation event or a series of neuromodulation events such that the one or more possible neuromodulation conflict(s) is/are avoided.

The method may be characterized in that one or more possible neuromodulation conflict(s) may be related to at least one of neuromodulation safety, hardware capabilities, software capabilities.

It is to be understood that both the foregoing general description and the following detailed description are exemplary and explanatory only and are not restrictive of the disclosed embodiments or the scope of the inventions as claimed. The concepts in this application may be employed in other embodiments without departing from the scope of the inventions.

BRIEF DESCRIPTION OF THE FIGURES

Further details and advantages of the disclosed embodiments shall now be disclosed in connection with the drawings. The accompanying drawings, which are incorporated in and constitute a part of this specification, illustrate several embodiments consistent with the disclosure and together with the description, serve to explain the principles of the disclosure. In the drawings:

Figure 8:
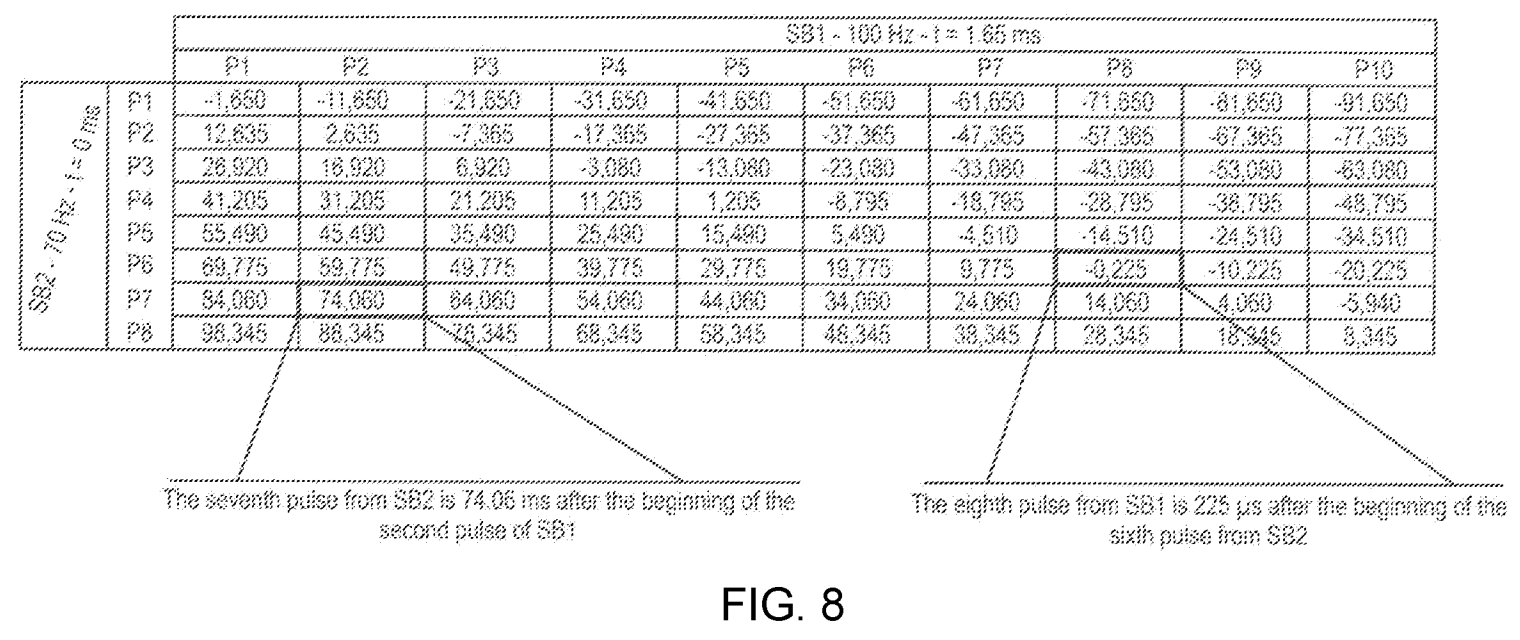

FIG. 8 depicts an exemplary embodiment of a pulse temporal distance matrix (in ms) during 100 ms for stimulation block 1 at 100 Hz starting at t=1.65 ms and stimulation block 2 at 70 Hz starting at t=0 ms, according to the present invention;

DETAILED DESCRIPTION

Reference will now be made in detail to exemplary embodiments, discussed with regards to the accompanying drawings. In some instances, the same reference numbers will be used throughout the drawings and the following description to refer to the same or like parts. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

Described herein are systems and methods for identifying and addressing conflicts in a neuromodulation event or series of neuromodulation events. Conflicts in neuromodulation or neurostimulation events or series of events may be related to neuromodulation safety, hardware capabilities, and/or software capabilities. For example, a conflict may be one or more of incompatible electrode configuration(s) EC between stimulation blocks (SB), incompatible stimulation block (SB) timing properties (such as e.g. frequency, pulse width, pulse shape, etc.), incompatible stimulation block (SB) amplitude properties, and/or may relate to the safety or comfortability of the neuro stimulation.

Figure 1:
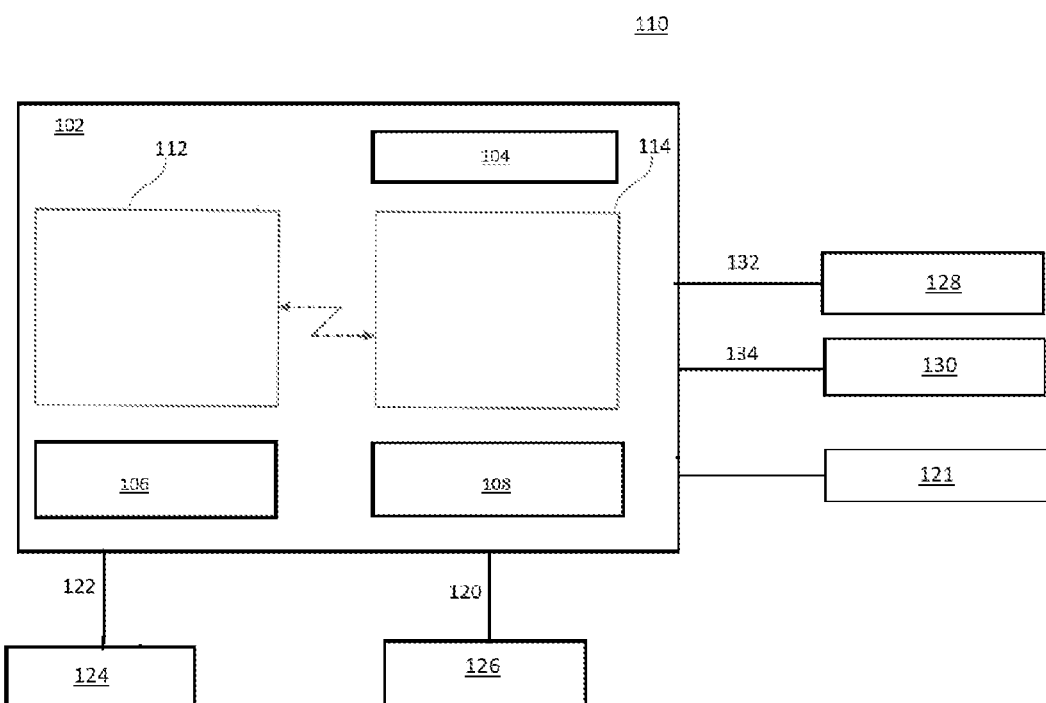
FIG. 1 depicts a schematic overview of an embodiment of the neuromodulation system according to the present invention, with which the method according to the present invention may be performed.
Figure 2:
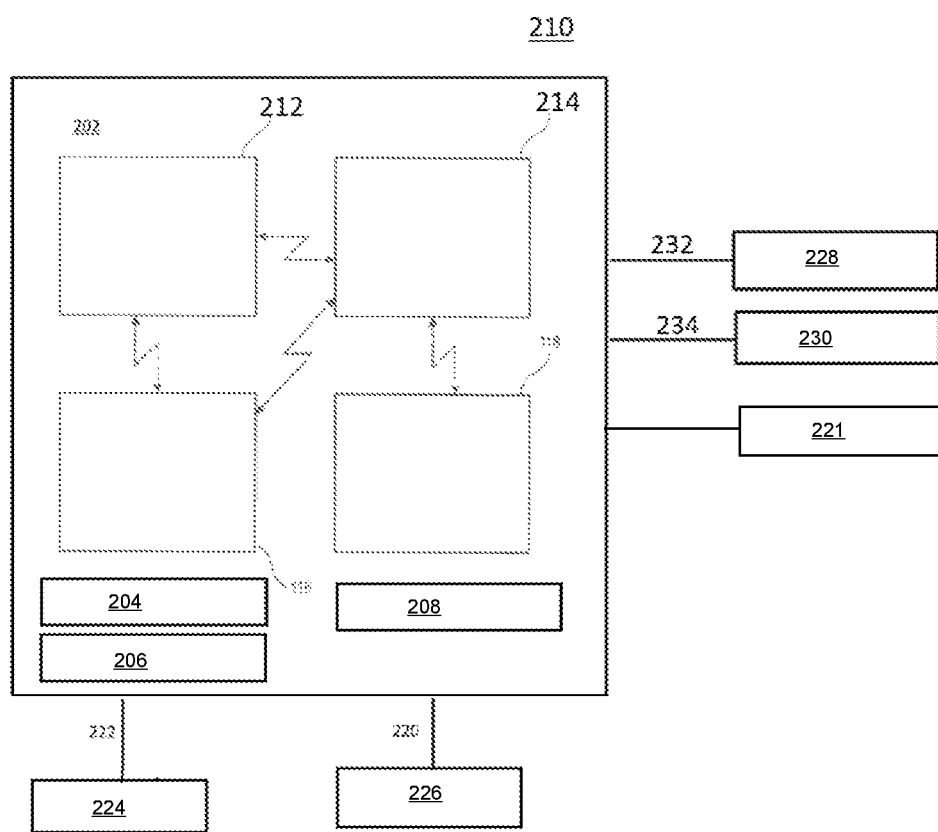
FIG. 2 depicts a schematic overview of a further embodiment of the neuromodulation system according to the present invention, with which the method according to the present invention may be performed.
Figure 3:
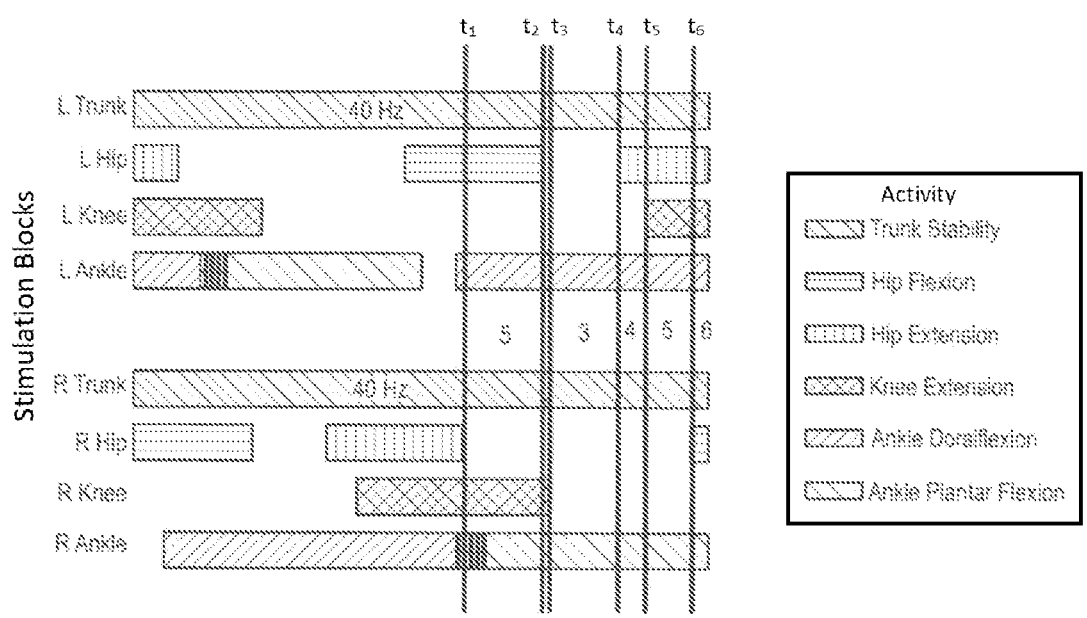
FIG. 3 depicts a schematic overview of a series of neuromodulation events.
Figure 4:
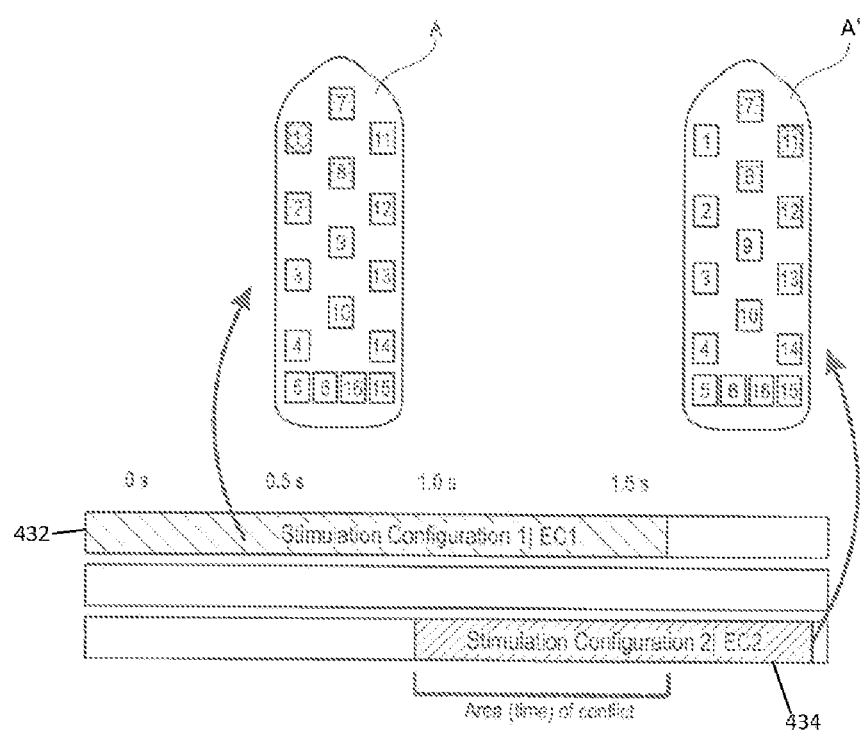
FIG. 4 depicts a schematic drawing of a series of neurostimulation events having the same dependency on certain electrodes of an array at a given time point, leading to conflict(s)
Figure 5:
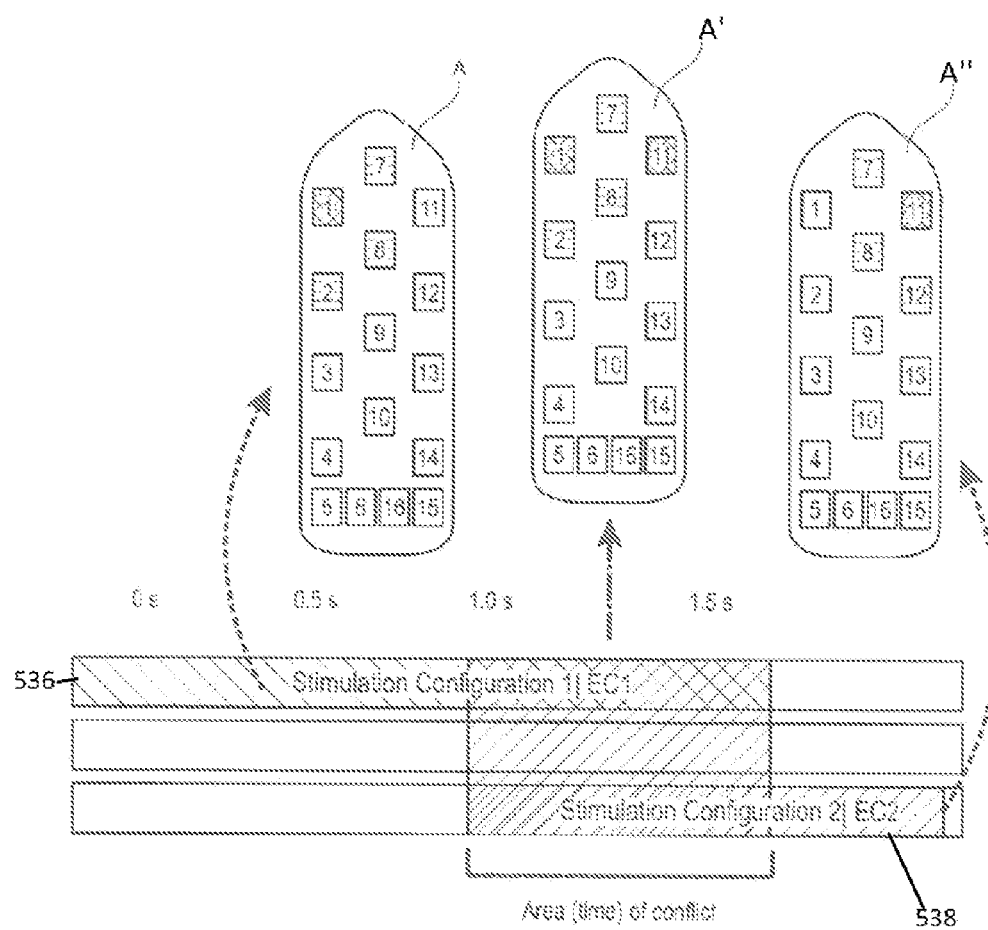
FIG. 5 depicts an exemplary embodiment of merging of two electrode configurations that would otherwise conflict, with the system disclosed in FIG. 2.
Figure 6:
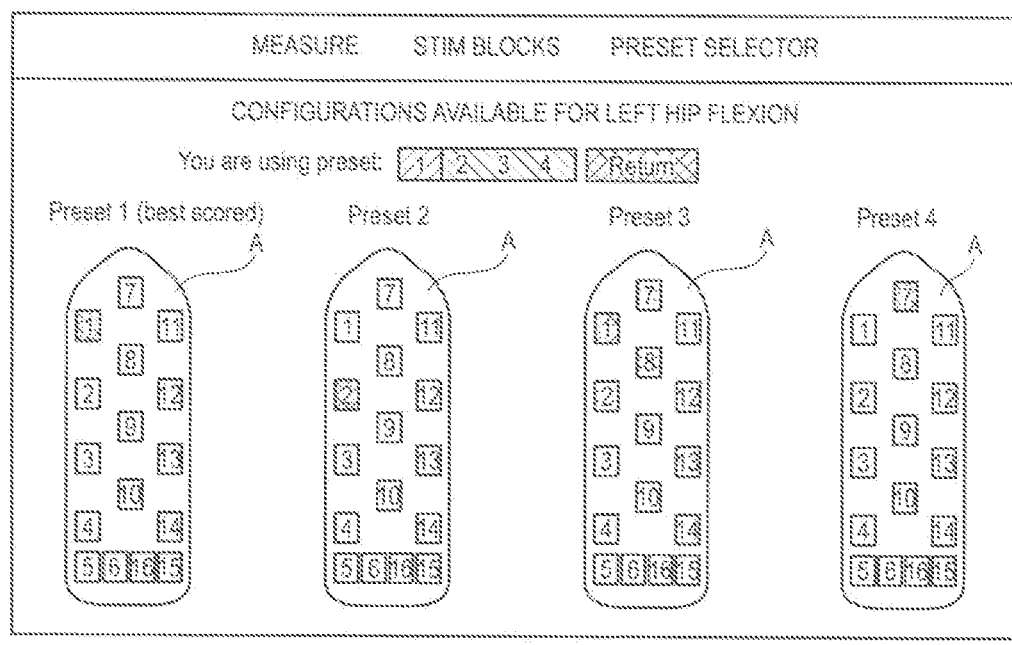
FIG. 6 depicts an exemplary embodiment of the visual output provided by the output means of the system disclosed in FIG. 2.
Figure 9:
FIG. 9 depicts an example of how the output means of the system could communicate an internal acceptable variation of the frequency, according to the present invention.

A neuromodulation event or series of neuromodulation events as shown in FIG. 3 may be analyzed by a neuromodulation system, such as the neuromodulation system shown in FIGS. 1 and 2. As shown in FIGS. 4 and 5, conflicts may be identified and resolution options may be provided by the system shown in FIG. 1 and FIG. 2. Resolution of a conflict may be provided manually, semi-automatically, or automatically using one or more of a plurality of solutions including, but not limited to, pulse interleaving, merging, amendment based on a Pseudo-Hamming Distance Criterion, and/or through the amendment of timing properties such as e.g. frequency, pulse width, pulse shape). In some aspects, resolution may be provided through the presentation of one or more preset neuromodulation events as shown in FIG. 6. In some aspects, identification of the conflict may be output via a visual display as shown in FIGS. 7, 10, 11, and 13. In additional aspects, spacing between pulses may be analyzed using the neuromodulation system shown in FIGS. 1 and 2 as seen by the matrix of FIG. 8. An internal acceptable variation to the end use of the frequency as used in the electrodes of the neuromodulation system shown in FIGS. 1 and 2 is shown in FIG. 9. In some aspects, the neuromodulation system shown in FIGS. 1 and 2 may include a training module (not shown). As shown in FIG. 12, such a training module may be used to inform a user of what stimulation frequency constraints exist while he/she is configuring the stimulation frequency. Exemplary methods as used by the neuromodulation system of FIGS. 1 and 2 for the identification and rectification of conflicts are shown in FIGS. 14 to 16.

FIG. 1 shows a schematic overview of an embodiment of the neuromodulation system 110 according to the disclosed embodiments, with which the methods according to the disclosed embodiments may be performed.

The system 110 may include a device 102 with an input module 112, an analyzing module 114, memory 104, a processor 106, and a communication subsystem 108, though other components and modules may also be included. For example, system 110 may further include a controller, a microcontroller, a telemetry system and/or a training device, and combinations thereof. In some aspects, as shown in FIG. 1, the device 102 may be coupled to a user input device 121, a display 124, an electrode array 126 comprising one or more electrodes, a pulse generator 128, and one or more sensors 130. While the device 102 is shown with a plurality of peripheral devices, the particular arrangement may be altered such that some or all of the components are incorporated in a single or plurality of devices as desired.

Collectively, the various tangible components or a subset of the tangible components of the neuromodulation system may be referred to herein as "logic" configured or adapted in a particular way, for example as logic configured or adapted with particular software, hardware, or firmware and adapted to execute computer readable instructions. The processors may be single core or multicore, and the programs executed thereon may be configured for parallel or distributed processing. The processors may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration, that is, one or more aspects may utilize ubiquitous, convenient, on-demand network access to a shared pool of configurable computing resources that can be rapidly provisioned and released with minimal management effort or service provider interaction. Clouds can be private, public, or a hybrid of private and public, and may include Infrastructure as a Service (IaaS), Platform as a Service (PaaS) and Software as a Service (SaaS). In some aspects, logic and memory may be integrated into one or more common devices, such as an application specific integrated circuit, field programmable gate array, or a system on a chip.

In some embodiments, device 102 may be any computing or mobile device, for example, mobile devices, tablets, laptops, desktops, PDAs, and the like, as well as virtual reality devices or augmented reality devices. Thus, in some embodiments, the device 102 may include a display and thus a separate display 124 or user input device 121 may not be necessary. In other aspects, the device may be coupled to a plurality of displays.

Memory 104 generally comprises a random-access memory ("RAM") and permanent non-transitory mass storage device, such as a hard disk drive or solid-state drive. Memory 104 may store an operating system as well as the various modules and components discussed herein. It may further include devices which are one or more of volatile, non-volatile, dynamic, static, read/write, read-only, random access, sequential access, location addressable, file addressable and content addressable.

Communication subsystem 108 may be configured to communicatively couple the modules within device 102 as well as communicatively coupling device 102 with one or more other computing and/or peripheral devices. Such connections may include wired and/or wireless communication devices compatible with one or more different communication protocols including, but not limited to, the Internet, a personal area network, a local area network (LAN), a wide area network (WAN) or a wireless local area network (WLAN). For example, wireless connections may be WiFi, Bluetooth®, IEEE 802.11, and the like.

As shown in FIG. 1, the system 110 comprises a device 102 with an input module 112. The input module 112 is configured and arranged for inputting a planned neuromodulation event or a series of neuromodulation events. The device 102 further comprises an analyzing module 114. The analyzing module 114 is configured and arranged for analyzing a neuromodulation event or a series of neuromodulation events.

As shown in FIG. 1, the input module 112 is connected to the analyzing module 114 as shown by the dotted by directional arrows. However, such a connection could equally apply to the other components and modules within device 102 all of which may be connected via wired and wireless connections. The connection between the input module 112 and the analyzing module 14 is a bidirectional connection. However, in an alternative embodiment, a unidirectional connection may be implemented (from the input module 112 to the analyzing module 114 and/or from the analyzing module 114 to the input module 112). In some embodiments, the input module 112 is connected to the analyzing module 114 by a wireless link facilitated through communication subsystem 108. In some aspects, one or more of the components and modules within the device 102 may be on the same or different devices, for example a plurality of modules may be located on the same chip.

Communication within the system 110 may occur locally or over one or more public/private/hybrid networks 120, 122, 132, 134 among others including one or more of a wireless network, a wired network, or a combination of wired and wireless networks. Suitable networks include, but are not limited to, public, private or hybrid networks including the Internet, a personal area network, a LAN, a WAN, or a WLAN. Information can further be received or transmitted over cellular networks either directly or through a base station and through the cloud. In other aspects input module 112 and analyzing module 114 may exist on the same processor. In further embodiments, they may exist in different devices and be communicatively coupled by a cable-bound connection. For example, in some aspects input module 112 and analyzing module 114 may exist on separate devices, with each device having a processor, memory and communication subsystem and the two devices may be commutatively coupled using a wired or wireless connection as described above.

In some embodiments, the input module 112 can input a planned neuromodulation event or a series of neuromodulation events. Such inputs may be received from one or more sources including, but not limited to, a user selecting one or more predesigned configurations or through input of a customized stimulation program. Further in some embodiments, the input module 112 can forward a planned neuromodulation event or a series of neuromodulation events to the analyzing module 114. Also, in some embodiments, the analyzing module 114 can analyze the planned neuromodulation event or a series of neuromodulation events regarding one or more possible neuromodulation conflict(s).

In some embodiments (not depicted in FIG. 1), system 110 could comprise more than one input module 112, and system 110 could comprise more than one analyzing module 114. The system 110 can be configured for a semi-automatic correction of a neuromodulation conflict. The system 110 can be configured for automatic correction of neuromodulation conflict. A neuromodulation conflict may be detected when the planned neuromodulation event or a series of neuromodulation events requires an impossible electrode configuration. More than one neuromodulation conflict can be detected when the planned neuromodulation event or a series of neuromodulation events requires an impossible electrode configuration. More than one neuromodulation conflict can be detected which are not related to electrode configuration.

Conflicts may be related to at least one of neuromodulation safety, hardware capabilities, software capabilities, and combinations thereof. For example, a conflict may be one or more of incompatible electrode configuration(s) EC between stimulation blocks SB, incompatible stimulation block SB timing properties (such as e.g. frequency, pulse width, pulse shape), incompatible stimulation block SB amplitude properties and/or may relate to the safety or comfortability of the neurostimulation. Identified conflicts may be addressed by one or more of amending the planned neuromodulation event or a series of neuromodulation events based on a Pseudo-Hamming Distance Criterion, allowing some pulse overlap and/or adapting the pulse shape; amending incompatible stimulation block SB timing properties (such as e.g. frequency, pulse width, pulse shape); replacing the planned neuromodulation event or series of neuromodulation events with one of alternative Presets instead; allowing custom pulse overlap rules; adapting the pulse shape; lowering the amplitude; assessing electrode stability; assessing the patient's response to stimulation; amending the VRAM available and/or the computation time; and/or issuing an alert and allowing the user to modify the programming.

FIG. 2 shows a schematic overview of a further embodiment of the neuromodulation system 210 according to the present invention, with which the methods according to the disclosed embodiments may be performed. The system 210 may include a device 202 with an input module 212, an analyzing module 214, memory 204, a correction module 116, an output means 118, processor 206, and a communication subsystem 208, though other components and modules may also be included. For example, a controller, a microcontroller, a telemetry system and/or a training device may be implemented in the system 210. In some aspects, as shown in FIG. 2, the device 202 may be coupled to a user input device 121, a display 224, an electrode array 226 comprising one or more electrodes, a pulse generator 228, and one or more sensors 230. While the device 102 is shown with a plurality of peripheral devices, the particular arrangement may be altered such that some or all of the components are incorporated in a single or plurality of devices as desired. Device 202 is a non-limiting example of device 102 and as such may include the same or similar components as described above.

In some embodiments, device 202 may be any computing or mobile device, for example, mobile devices, tablets, laptops, desktops, PDAs, and the like, as well as virtual reality devices or augmented reality devices. Thus, in some embodiments, the device 202 may include a display and user input device and thus a separate display 224 or user input device 221 may not be necessary.

Memory 204 generally comprises a random-access memory ("RAM") and permanent non-transitory mass storage device, such as a hard disk drive or solid-state drive. Memory 204 may store an operating system as well as the various modules discussed herein. It may further include devices which are one or more of volatile, non-volatile, dynamic, static, read/write, read-only, random access, sequential access, location addressable, file addressable and content addressable.

Communication subsystem 208 may be configured to communicatively couple the modules within device 202 as well as communicatively coupling device 202 with one or more other computing devices. Such connections may include wired and/or wireless communication devices compatible with one or more different communication protocols including, but not limited to, the Internet, a personal area network, a local area network (LAN), a wide area network (WAN) or a wireless local area network (WLAN). For example, wireless connections may be WiFi, Bluetooth®, IEEE 802.11, and the like.

The system 210 comprises the structural and functional features as disclosed for neuromodulation system 110 disclosed in FIG. 1. The corresponding references are indicated as 200+x (e.g. input module 212 or memory 204). Accordingly, device 202 may share features with device 102 described above, memory 204 may share features with memory 104 described above, processor 206 may share features with processor 106 described above, and communication subsystem 208 may share features with communication subsystem 108.

The neurostimulation system 210 may further comprise a correction module 116. In some embodiments, the neurostimulation system 210 comprises more than one correction module 116. In some embodiments, the neurostimulation system 210 further comprises output means 118. The correction module 116 is connected to the input module 212 and the analyzing module 214.

In some embodiments, the connection between the correction module 116 and the input module 212 and the correction module 116 and the analyzing module 214 is a bidirectional and wireless connection through communication subsystem 208. Communication within the system 210 may occur locally or over one or more public/private/hybrid networks 220, 222, 232, 234 including one or more of a wireless network, a wired network, or a combination of wired and wireless networks. Suitable networks include, but are not limited to, public, private or hybrid networks including the Internet, a personal area network, a LAN, a WAN, or a WLAN. Information can further be received or transmitted over cellular networks either directly or through a base station and through the cloud. In other aspects, input module 212, analyzing module 214, correction module 116, and output means 118 may exist on the same processor. In further embodiments, input module 212, analyzing module 214, correction module 116, and output means 118 may exist in one or more devices and be communicatively coupled by a cable-bound connection. For example, in some aspects input module 212, analyzing module 214, correction module 116, and output means 118 may exist on separate devices, with each device having a processor, memory and communication subsystem and the two or more devices may be commutatively coupled using a wired or wireless connection as described above.

As depicted in FIG. 2, the output means 118 may be connected to the analyzing module 214. In some embodiments, the output means 118 is an output module. In some embodiments, the connection between the output means 118 and the analyzing module 214 is a bidirectional and wireless connection. However, in an alternative embodiment, a unidirectional and/or cable-bound connection between the output means 118 and the analyzing module 214 may be implemented. In an alternative embodiment, the output means 118 may additionally be connected to the input module 212 and/or the correction module 116 (via bidirectional or unidirectional connection and/or wireless or cable-bound connection).

In some embodiments, the correction module 116 amends the planned neuromodulation event or a series of neuromodulation events. In some embodiments, when a neurostimulation conflict is detected, the neuromodulation event or a series of neuromodulation events is/are amended such that the neuromodulation conflict is avoided as described in further detail below. In some embodiments, the output means 118 provides at least partially a visual output of the analysis performed by the analyzing module 214. In an alternative embodiment, the output means 118 provides, at least partially, the planned neuromodulation event or a series of neuromodulation events and/or the neuromodulation conflict(s) and/or the correction of the planned neuromodulation event or a series of neuromodulation events. In some aspects, the visual output can be sent to the display 224.

In some embodiments (not shown in FIG. 2), system 210 can also include multiple correction modules, and system 210 may also comprise multiple output means. The system (e.g. system 110 and/or system 210) may perform a method for performing neuromodulation comprising at least the following steps: receiving a planned neuromodulation event or a series of neuromodulation events, analyzing the planned neuromodulation event or a series of neuromodulation events, wherein the analyzing includes the analysis whether the planned neuromodulation event or a series of neuromodulation events comprises one or more possible neuromodulation conflict(s).

In some embodiments, the method may further comprise correcting the neuromodulation event or a series of neuromodulation events such that the one or more possible neuromodulation conflict(s) is/are avoided.

In general, the system (e.g. system 110 and/or system 210) and the method may avoid and/or solve the conflict(s) may by amending incompatible electrode configuration(s) EC between stimulation blocks SB and/or amending incompatible stimulation block SB timing properties (such as e.g. frequency, pulse width, pulse shape) and/or by amending incompatible stimulation block SB amplitude properties and/or by assessing the safety or comfortability of the neurostimulation and/or by amending software limitations.

FIG. 3 shows a schematic overview of a series of neuromodulation events of different stimulation blocks SB. The series of neuromodulation events can also be referred to as stimulation program and/or stimulation partiture.

A stimulation block may determine an electrode configuration and/or stimulation configuration, and/or an amplitude/intensity of stimulation and a pulse train, wherein a pulse train may be defined as a temporal arrangement of stimulation events. Different stimulation blocks need to be stimulated during movement (e.g. a gait cycle) consequentially and/or at least partially simultaneously with different pulsed electrical waveforms at different frequencies and amplitudes, sometimes with different pattern of pulses, in order to reproduce a movement, e.g. a gait cycle comparable to a healthy subject.

As illustrated in FIG. 3, the series of neuromodulation events includes multiple time segments (indicated by the vertical lines $t_1$, $t_2$, $t_3$, $t_4$, $t_5$, $t_6$). In some embodiments, the stimulation blocks SB are Left (L) Trunk, Left (L) Hip Flexion, Left (L) Hip Extension, Left (L) Knee, Left (L) Ankle Flexion, Left (L) Ankle Extension, Right (R) Trunk, Right (R) Hip Flexion, Right (R) Hip Extension, Right (R) Knee, Right (R) Ankle Flexion, Right (R) Ankle Extension.

In each time segment, the combination of active stimulation blocks SB each targeting a specific muscle group may be fixed. In some embodiments, the first time segment $t_1$ drawn has 5 stimulation blocks SB active simultaneously (Left (L) Trunk and Right (R) Trunk counted as one). In some embodiments, the second time segment $t_2$ drawn has 4 stimulation blocks SB active simultaneously (Left (L) Trunk and Right (R) Trunk counted as one). In some embodiments, the third time segment $t_3$ drawn has 3 stimulation blocks SB active simultaneously (Left (L) Trunk and Right (R) Trunk counted as one). In some embodiments, the fourth time segment $t_4$ drawn has 4 stimulation blocks SB active simultaneously (Left (L) Trunk and Right (R) Trunk counted as one). In some embodiments, the fifth time segment $t_5$ drawn has 5 stimulation blocks SB active simultaneously (Left (L) Trunk and Right (R) Trunk counted as one). In some embodiments, the sixth time segment $t_6$ drawn has 6 stimulation blocks SB active simultaneously (Left (L) Trunk and Right (R) Trunk counted as one). As shown in the legend, each stimulation block is directed towards stimulating a particular action or activity.

FIG. 4 shows a schematic drawing of a series of neurostimulation events having the same dependency on certain electrodes of an array (see e.g. electrode array 226 in FIG. 2) at a given time point, with the dependency of the first stimulation block shown at A and the second stimulation block shown at A', leading to a conflict, where A and A' are different configurations of the same electrode array.

In some embodiments, the neuromodulation system 210 disclosed in FIG. 2 is applied. FIG. 4 illustrates two electrode configurations EC1, EC2 (also referred to as stimulation configurations) and an electrode array A, A' comprising 16 electrodes 1-16. In an alternative embodiment, the electrode array A, A' may comprise fewer or more than 16 electrodes.

In some embodiments, the series of neurostimulation events comprises two different electrode configurations EC1 and EC2 for two different stimulation blocks SB1 432 and SB2 434. Stimulation block 1 432 is requested to be stimulated according to electrode configuration 1 EC1. Stimulation block 2 434 is requested to be stimulated according to electrode configuration 2 EC2. The electrodes used by the stimulation configuration are shown in hatching with A and A' indicating different patterns of use in the same array. For example, in array A, as shown by the various hatch patterns, electrodes 1, 2, 7, and 8 will be used for stimulation configuration 1. As shown in A', electrodes 7, 8, 11 and 12 will be used for stimulation configuration 2. Thus, FIG. 4 illustrates that the two electrode configurations EC1 and EC2 both use electrode 7 and electrode 8 of the electrode array.

As shown in the stimulation configuration, the two stimulation blocks SB1 432, SB2 434 have overlapping periods of use from 1.0 s to 1.5 s. The analyzing module 114 of the system 110 would thus detect a neuromodulation conflict of the planned series of neuromodulation events. Correction module 116 of the system 210 may amend the planned series of neuromodulation events such that the neuromodulation conflict is avoided. Correction may be made manually, automatically, or semi-automatically.

In some embodiments (not shown in FIG. 4), the correction module 116 amends the planned series of neuromodulation events by providing at least one alternative electrode configuration EC (see, e.g. FIG. 6). Alternatively, and/or additionally, the correction module 116 could amend the planned series of neuromodulation events by keeping the electrode configurations EC1 and EC2 but interleaving pulses, thus by avoiding pulse overlap. If the stimulation pulses are interleaved in a way that fully avoids overlap, then the shared electrodes will not be requested by both stimulation block 1 and stimulation block 2 at the same time. This pulse interleaving could be done with any method avoiding pulse overlap, e.g. Pulse Train Scheduling. Alternatively, and/or additionally, the correction module 116 could amend the planned series of neuromodulation events by merging electrode configuration EC1 and electrode configuration EC2, cf. FIG. 5.

FIG. 5 shows an example of merging of two electrode configurations EC1 and EC2 that would conflict as electrodes 7 and 8 would be used in both configurations from 1.0 s to 1.5 s as shown in A and A". In order to overcome this conflict, the system 210 disclosed in FIG. 2 merges two electrode configurations EC1 and EC2 as shown at A' via the correction module 116 that amends the planned series of neuromodulation events.

In some embodiments, the correction module 116 provides an automated merging of electrode configurations EC1 and EC2 and balance amplitudes. In some embodiments, during the period of overlap, the electrode configurations EC1 and EC2 are merged. The merged stimulation block SB delivers a single stimulation, exciting both the nerve fibers targeted by stimulation block SB1 536 and the nerve fibers targeted by stimulation block SB2 538 at the same time.

However, the achieved stimulation for the nerve fibers targeted by stimulation block SB1 and for the nerve fibers targeted by stimulation block SB2 may depend on both the amplitude and on the frequency used. Thus, merging the electrode configurations EC1, EC2 of both stimulation blocks SB1, SB2 may be implemented if the frequencies and amplitudes of both stimulation blocks SB1, SB2 match, are nearly identical, or are identical.

In some aspects, the correction module 116 may amend the neuromodulation event or series of neuromodulation events by merging the electrode configurations if the conflict between the planned neuromodulation event or series of neuromodulation events meets specific criteria. For example, the stimulation events may be merged if the planned event meets particular criteria. In some embodiments, the stimulation configuration may be merged if a particular tolerance margin is obtained. In some embodiments, the stimulation configurations can be merged if at least one of the frequency of stimulation block SB1 is within a ±15 Hz of the frequency of stimulation block SB2 or the amplitude of stimulation block SB1 is within a ±2 mA of the amplitude of stimulation block SB2.

Depending on the stimulation frequencies used for stimulation block SB1 and stimulation block SB2, only part of their pulses may overlap in time. Therefore, the electrode sharing conflict only emerges during those periods of pulse overlap. In some aspects, the system may therefore merge both electrode configurations EC1, EC2 into one configuration when such a conflict arises, i.e. for some specific colliding pulses.

The amplitudes can be balanced to preserve either the charge balancing or the electrical field. Summing the current on the shared electrode will preserve the charge balancing but may heavily impact the electrical field. For instance, in the example shown in FIG. 5: stimulation block SB1 uses electrode 1 as a cathode at −9 mA and electrode 2, electrode 7 and electrode 8 as anodes at 3 mA each. Stimulation block SB2 uses electrode 11 as a cathode at −18 mA and electrode 12, electrode 7 and electrode 8 as anodes at 6 mA each. Summing the current will result in:

Electrode 1: −9 mA
Electrode 11: −18 mA
Electrode 2: 3 mA
Electrode 12: 6 mA
Electrodes 7, 8: 9 mA Instead, choosing to use the average of the current on the shared electrode would result in:

Electrode 1: −9 mA
Electrode 11: −18 mA
Electrode 2: 3 mA
Electrode 12: 6 mA
Electrodes 7, 8: 4.5 mA The electrical field is closer to the electrical field generated by each stimulation block SB taken separately but the charge balancing is lost. However, if the amount of corrupted pulse for stimulation block SB1 and stimulation block SB2 is sufficiently low, e.g. below a threshold, then the grounding time could accommodate for the loss of charge balancing.

FIG. 6 shows an example of the visual output of particular electrode configurations a user can select as provided by the output means 118 of the system 210 disclosed in FIG. 2. In some embodiments, the output means 118 provides different electrode configurations EC to achieve a certain muscular response.

For example, in the event of a conflict, as disclosed in FIG. 4, the stimulation configuration inputted may be replaced with one of alternative Presets instead. Thus, in some embodiments, the output means 118 provides (at least partially) a visual output of the correction of the conflict of the planned series of neuromodulation events disclosed in FIG. 4. In some embodiments, four Presets may be available, out of a maximum amount of Presets, which may be five. Moreover, using a graphical user interface, a more advanced user could also replace the inputted stimulation configuration with a custom electrode configuration. Alternatively, as for the solution merging electrode configurations, the system could also use an alternative stored Preset stimulation configuration for the pulses of stimulation block SB1 and stimulation block SB2 that overlap in time.

In general, the output means 118 and the analyzing module 214 may function online or offline as each pulse can be linked to an index. Each pulse needing a non-default stimulation configuration may have its index and the associated Preset stimulation configuration transmitted to the stimulation system along with the stimulation program.

In addition to conflicts depending on electrode configurations, the stimulation partiture could also include stimulation blocks that are intended to be active at the same time yet use conflicting properties such as their frequencies or pulse shape. Moreover, a method avoiding pulse overlap may be applied to limit the interference between the stimulation blocks. Each time segment can be translated into an input combination for the method avoiding pulse overlap, (e.g. 20, 40, 75 Hz). The method avoiding pulse overlap may find a solution avoiding pulse overlap. However, some combinations may not have a solution and are marked as non-solutions. Thus, if such a combination is inputted on the partiture by the user, it will result in a conflict as shown below.

Figure 7:
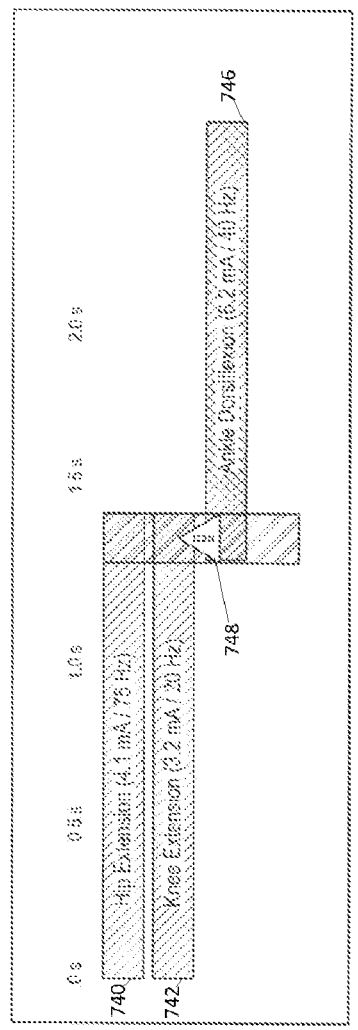
FIG. 7 depicts an exemplary embodiment of incompatible stimulation block timing properties, analyzed with the system disclosed in FIG. 2, provided as visual output by the output means.

FIG. 7 shows visual output provided by the output means 118 of an analysis performed by the analyzing module 114, 214, of the system 110, 210 disclosed in FIGS. 1 and 2. In some embodiments, the system 210 may analyze and correct pulse overlap. In an alternative embodiment, the system 110, 210 may analyze and correct inter alia pulse overlap.

FIG. 7 illustrates an example of incompatible stimulation block SB timing properties, analyzed with the system 110, 210 disclosed in FIGS. 1 and 2 provided as visual output by the output means 118.

In some embodiments, the system 110, 210 is configured for avoiding pulse overlap, and is applied to limit the interference between the stimulation blocks SB1 (including the hip and knee extension stimulation) and SB2 (including the ankle dorsiflexion stimulation). As shown at 748, an alert is shown indicating a conflict prior to 1.5 s.

In some aspects, the correction module 116 may provide a plurality of solutions to correct or overcome the conflict. For example, each time segment could be translated into an input combination avoiding pulse overlap (e.g. 20, 40, 75 Hz). However, this solution may not work for all combinations. In other aspects, the correction module 116 may amend the planned neuromodulation event or a series of neuromodulation events based on a Pseudo-Hamming Distance Criterion, allowing some pulse overlap and/or adapting the pulse shape. In other words, in some embodiments, the conflict is avoided by amending incompatible stimulation block SB timing properties (such as e.g. frequency, pulse width, pulse shape) as discussed in further detail below.

Pseudo-Hamming Distance Criterion

For example, a Pseudo-Hamming distance criterion could be applied to determine close-by inputs which are acceptable. In some embodiments, the above-described example with a unique pulse shape and the frequencies (e.g. 20, 40, 75 Hz) is considered. In some embodiments, it is assumed that the possible programmable input frequencies are 20, 40, 50 and 75 Hz. One of the stimulation blocks SB from the combination (e.g. 20, 40, 75 Hz) could have its frequency replaced with a close-by frequency. To determine the close-by frequencies, a pseudo-Hamming distance criterion is used by the system 110, 210:

Changing 1 element by a step of 1 within the list of inputs results in a distance of 1. e.g.
  a. changing 40 to 50 Hz.
  b. changing 75 Hz to 50 Hz.

Changing 2 elements by a step of 1 within the list of inputs or changing 1 element by a step of 2 within the list of inputs results in a distance of 2. e.g.
  a. Changing 40 to 50 Hz and changing 75 to 50 Hz.
  b. Changing 20 to 50 Hz.

Moreover, two modifications with the same Pseudo-Hamming distance may not be equally favorable because the inputs may not be equally spaced. For instance, changing 40 to 50 Hz could be more favorable than changing 75 Hz to 50 Hz. A weighing factor could be taken into account to represent the distance between the steps, i.e. the size of the step. In the end, if the combination (e.g. 20, 40, 75 Hz) does not have a solution avoiding pulse overlap (or meeting an overlap requirement, e.g. 5% of the total number of pulses may overlap), but the close-by combination (e.g. 20, 50, 75 Hz) does have a solution (e.g. it has only 3% of the pulses overlapping), then the Ankle Dorsiflexion frequency of 40 Hz may be replaced with 50 Hz.

Any kind of equation accounting for the frequencies, but also the pulse shape or other parameter may be used to quantify the distance between combinations of input parameters, e.g. frequency input combinations.

Alternatively, the system 110, 210 could propose to replace "flexor" continuous high-frequency stimulation blocks SB by burst stimulation blocks SB which are more (electric) power efficient and could potentially increase stimulation efficacy as well.

Allowing Some Pulse Overlap

For a variable frequency stimulation algorithm allowing custom pulse overlap rules, the following could be used. For example, if the electrode configurations EC do not overlap (i.e. if there is no electrode shared between the stimulation blocks SB), some overlap between stimulation events and/or pulses may be allowed. For instance, the stimulation phase of each stimulation block SB may be allowed to overlap with the post-stimulation phase of any other SB. Thus, the combination (20, 40, 75) Hz, which may not have any solutions avoiding pulse overlap, may now have solutions with partial and/or limited overlap. The user can be presented with options indicating the percentage of overlapping pulses for the different frequencies involved in the desired input combination. Alternatively, the solution may be selected automatically based on predefined criteria, such as selecting the solution with the lowest cumulative overlap percentage.

Adapting the Pulse Shape

If a combination of stimulation blocks SB does not have a solution respecting the pulse overlap requirements, the timeline may be too crowded. An exemplary approach to free up time on the timeline is to reduce the pulse duration by adapting its shape. For instance, for biphasic pulses, the post-stimulation phase could be shortened or dropped altogether.

The hardware may not be able to deliver the stimulation if the amplitude of the planned neuromodulation event or series of neuromodulation events exceeds the hardware capability. Especially in the case of overlapping pulses, partially or fully, the sum of the amplitude from the overlapping pulses may exceed the hardware capability. Additionally, and/or alternatively, the conflict(s) may be based on incompatible stimulation block SB amplitude properties.

The correction module 116 of the neuromodulation system 210 (see e.g. FIG. 2) may amend the planned neuromodulation event or a series of neuromodulation events at least partially based on lowering the amplitude.

Lowering the Amplitude

Additionally, and/or alternatively, the amplitude of one or of several of the stimulation blocks SBs involved in the conflict(s) could be lowered to resolve the conflict.

For example, the conflict may be resolved if the amplitude of all stimulation blocks SBs may all be lowered with the same percentage leading to a total current that is within the current capabilities of the stimulation engine.

Digital-to-Analogue Converter Setting Time

The digital-to-analogue converter used to deliver a precise stimulation current/voltage needs a finite amount of time to change its output value to the newly programmed setting.

In one embodiment, a digital-to-analogue-converter could need up to 200 µs to 1 ms to change a pulse generator output current from one a previous programmed value to the newly desired one. To assess if the digital-to-analogue-converter involved in the neurostimulation program will always have sufficient time to change their output, the following method could be applied:

For all the combinations of two stimulation blocks SB sharing the same current/voltage source, at least one of compute the pulse distance matrix of the two stimulation blocks SB, or check if any value is below a threshold (e.g. 200 µs, 400 µs or 1 ms).

The pulse distance matrix represents the temporal distance between pulse i of stimulation block SB1 and pulse j of stimulation block SB2. An example computed for a stimulation block SB1 at 100 Hz, starting at t=1.65 ms; and a stimulation block 2 at 70 Hz starting at t=0 ms is provided in FIG. 8.

FIG. 8 illustrates that both stimulation blocks SB1, SB2 are using 300 µs stimulation phase, 50 µs inter-phase delay, 900 µs post-stimulation phase. In some embodiments, the threshold to determine if a digital-to-analogue converter has enough time to change its output can be fixed or computed with the involved change of the digital-to-analogue converter output level through a digital-to-analogue converter model applied by the correction module 116. For instance, changing the output from the minimum to half of the maximum may not take as long as changing the output from the minimum (e.g. zero) to the maximum (e.g. full-scale). If the two stimulation blocks SB1, SB2 sharing a current/voltage source have pulses too close in time, their amplitudes could be lowered/modified in order to ensure that the digital-to-analogue converter output has enough time to reach its final value. Alternatively, if the pulse scheduling method can accommodate it, alternative timing solutions can be looked for and selected to increase the distance between the pulses and to ensure that the digital-to-analogue converter output will have enough time to reach its final value. Yet another alternative is to allow a certain amount of pulse corruption that may happen if the digital-to-analogue converter has not enough time to settle its output to the newly desired level, and consequently, the digital-to-analogue converter is still settling while the stimulation pulse is already output.

Embodiments of this disclosure provide solutions where a particular amount of pulse corruption is allowed, for example, if each stimulation block SB in a solution complies with a maximum allowable corruption percentage of all its pulses. Further, the conflict(s) may be avoided by amending and/or assessing the safety or comfortability of the neurostimulation. In some embodiments, each patient may be different and may have a different reaction to neuromodulation, e.g. stimulation.

This reaction may be modelled and/or measured and used to assess the safety or comfortability of a stimulation program by computing e.g. the electrical field resulting from the neurostimulation, the applied charge density or in case of comfortability, measuring the response of a patient to stimulation. A threshold may be applied to those parameters to assess if the neurostimulation is within predefined safety or comfortability limits (e.g. preventing too intense, uncomfortable stimulation).

Grounding Time

The charges injected in the tissue must be recovered through active or passive recuperation to ensure electrode stability and to keep stimulation currents/voltages within the compliance ranges of the pulse generators. More specifically, grounding could help to prevent that an electrode potential exceeds the water window so that electrode stability can be guaranteed. The passive recuperation may be achieved through grounding for a particular amount of time: i.e. grounding the electrodes when no stimulation pulse is output. However, charge recovery is not instantaneous, but the amount of grounding time may be assessed beforehand.

If it is verified that the available grounding time of all timing solutions used in a partiture is sufficient, the stimulation program may be deemed permissible and may be used by the stimulation system (e.g. IPG), else, an alternative stimulation program may be proposed where the partiture does comply with a minimum amount of grounding time for each electrode. Moreover, the distribution of the grounding time in time may also be taken into account to assess if a solution ensures electrode stability during stimulation.

Comfortability

The comfortability could also be assessed by measuring/evaluating the patient's response to a stimulation (e.g. the response to a stimulation block SB, a time segment or a complete partiture). This additional information may be used to further customize the allowable stimulation for the patient. For instance, the ramp up speed used to ramp up the amplitude at the beginning of a stimulation block, and to limit the torque in a joint movement, could be adapted for each patient based on his feedback (e.g. a maximum allowable amplitude ramping speed may be set for each joint of a patient).

Further, the conflict(s) could be avoided by amending software limitations. In some embodiments, the computational power of implantable devices is usually limited because of their low-power properties. To output a stimulation program/partiture, a certain number of steps could be required based on the software implementation. The stimulation program/partiture may create conflicts within the software capabilities which may require a change of the stimulation parameters. The impact of the stimulation program/partiture on the implantable device software can also be assessed beforehand and conflicts can be avoided before the program is released to the stimulation system. Further, the conflict(s) could be avoided by amending the VRAM available and/or the computation time.

VRAM Available

Especially if the stimulation program/partiture is composed of many stimulation blocks, the implantable device might not be able to output the stimulation program because it exceeds its memory capacity. A limitation on the length of the stimulation program/partiture and on the number of used stimulation blocks can be added to the checking criteria to prevent this memory overflow error.

Computation Time

Moreover, to deliver the stimulation a controller, e.g. an implanted microcontroller may perform multiple operations, e.g. sending messages, accessing a look-up table, etc. Usually, the controller scheduling rules are "best-effort": if two tasks have to be performed together, one will be delayed. Those delays may be impacting the neurostimulation, e.g. a pulse could be delayed changing the timing of the stimulation. A minimum amount of time for each task could be implemented. If the stimulation program/partiture inputted results in scheduling conflicts (e.g. overlapping tasks), then the partiture is adapted in order to attribute this minimum amount of time for each task.

In one embodiment, the neuromodulation system 110, 210, in some embodiments the output means 118, comprises a graphical-user-interface for the user to create stimulation partitures. The output means 118 provides at least two pathways for resolving arising conflict(s), including at least one of automatically suggesting and applying an alternative stimulation program, or providing information to the user so that the user can manually perform corrections.

Automatically Providing Alternative Stimulation Program

The system 110, 210 may automatically apply modifications to the stimulation blocks SB/partiture. For instance, the amplitude, the frequency or the pulse width may be changed automatically.

FIG. 9 depicts an exemplary indication of an acceptable variation of the frequency to the end-user. This indication can be communicated by the output means 118 of the system 210. In some embodiments, the correction module 116 may feature a frequency margin/tolerance that, in case of conflicts, it may select any frequency between 72 and 88 Hz to accommodate the user's desired partiture. The frequency margin/tolerance can be visualized as a ±10% indicator while the user selects the frequency on a graphical user interface, provided by the output means 118. In this approach, the user is not shown when conflicts occur and the user is not asked to perform an action. The system 110, 210 can be provided enough freedom and flexibility in user-defined stimulation parameters to find workable solutions.

Semi-Manual Conflict Resolution

Figure 10:
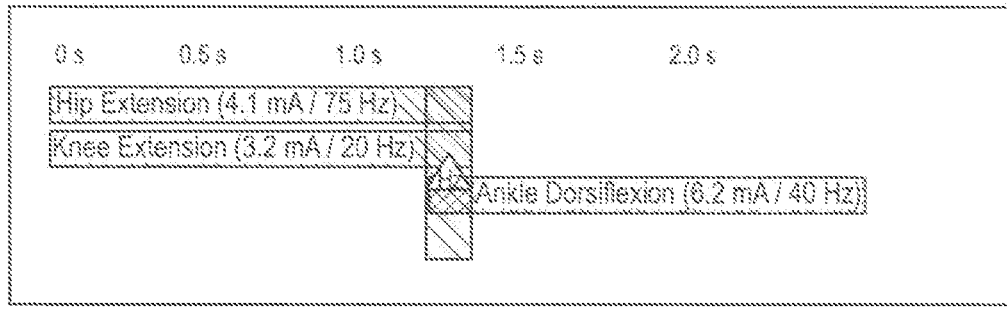
FIG. 10 depict an exemplary embodiment of how the output means of the system could communicate a conflict and an instruction how to resolve this conflict, according to the present invention.

Rather than fully-automatic resolution of conflicts, the output means 118 may provide visual feedback to the user that a conflict exists (or did exist) and a solution needs to be applied (or was provided automatically). Such feedback could be visualized directly on a graphical-user-interface through which the user is creating the stimulation partiture. Possible visualizations and embodiments are shown in FIGS. 7 and 10.

Figure 11:
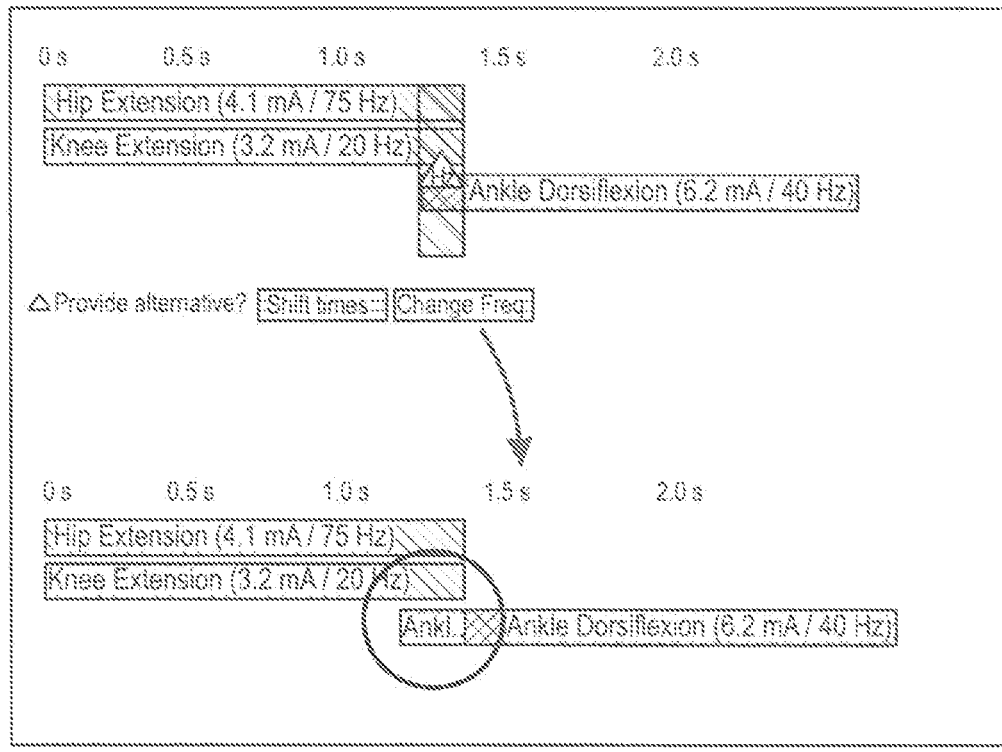
FIG. 11 depicts an exemplary embodiment of how the output means of the system could communicate a conflict and two possible strategies that can be applied by the system to resolve the conflict.
Figure 12:
FIG. 12 depicts an exemplary embodiment of how the output means provide visible information on what stimulation frequency constraints exist to a user while he/she is configuring the stimulation frequency.

FIG. 11 illustrates that there are various possible embodiments with different degrees of manual control to the user. For example, the user may be presented options by the output means 118 and he/she may select the desired approach. In some embodiments, the user can be presented two possible strategies/algorithms the correction module 116 can apply to resolve the conflict. Here, the user picks the option to change frequencies after which the correction module 116 creates a second Ankle Dorsiflexion that, during the overlap period, employs a different frequency that is compatible with the other two blocks (the other two being: Hip Extension and Knee Extension).

Stimulation Conflict Prevention

Moreover, rather than combatting the effects, stimulation conflicts could also be prevented from arising initially. This may be implemented by educating the user while he or she is creating stimulation partitures. Hints or instruction messages could be provided using so-called "Just-in-time" information paradigms.

One exemplary embodiment is shown in FIG. 12 when the user is taught what stimulation frequency constraints exist while he/she is configuring the stimulation frequency. In some embodiments, the output means 118 provides a note to instruct the user about the system 110 limitation. In this case, the user must choose a frequency accordingly.

Figure 13:
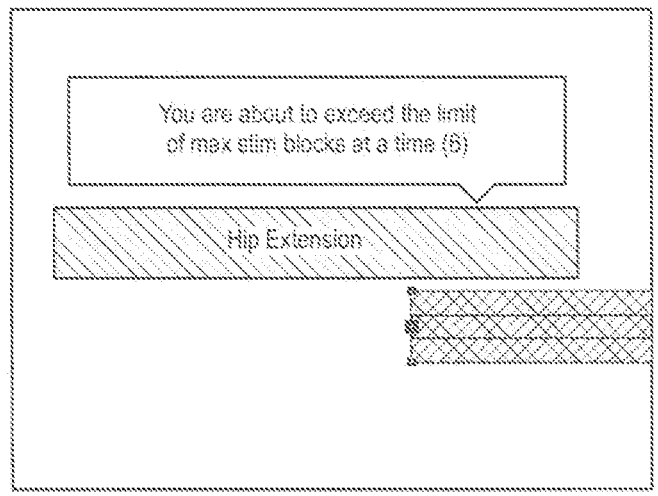
FIG. 13 depicts an exemplary embodiment of how the output means provide visible information on how a user is informed about the systems limitations.
Figure 14:
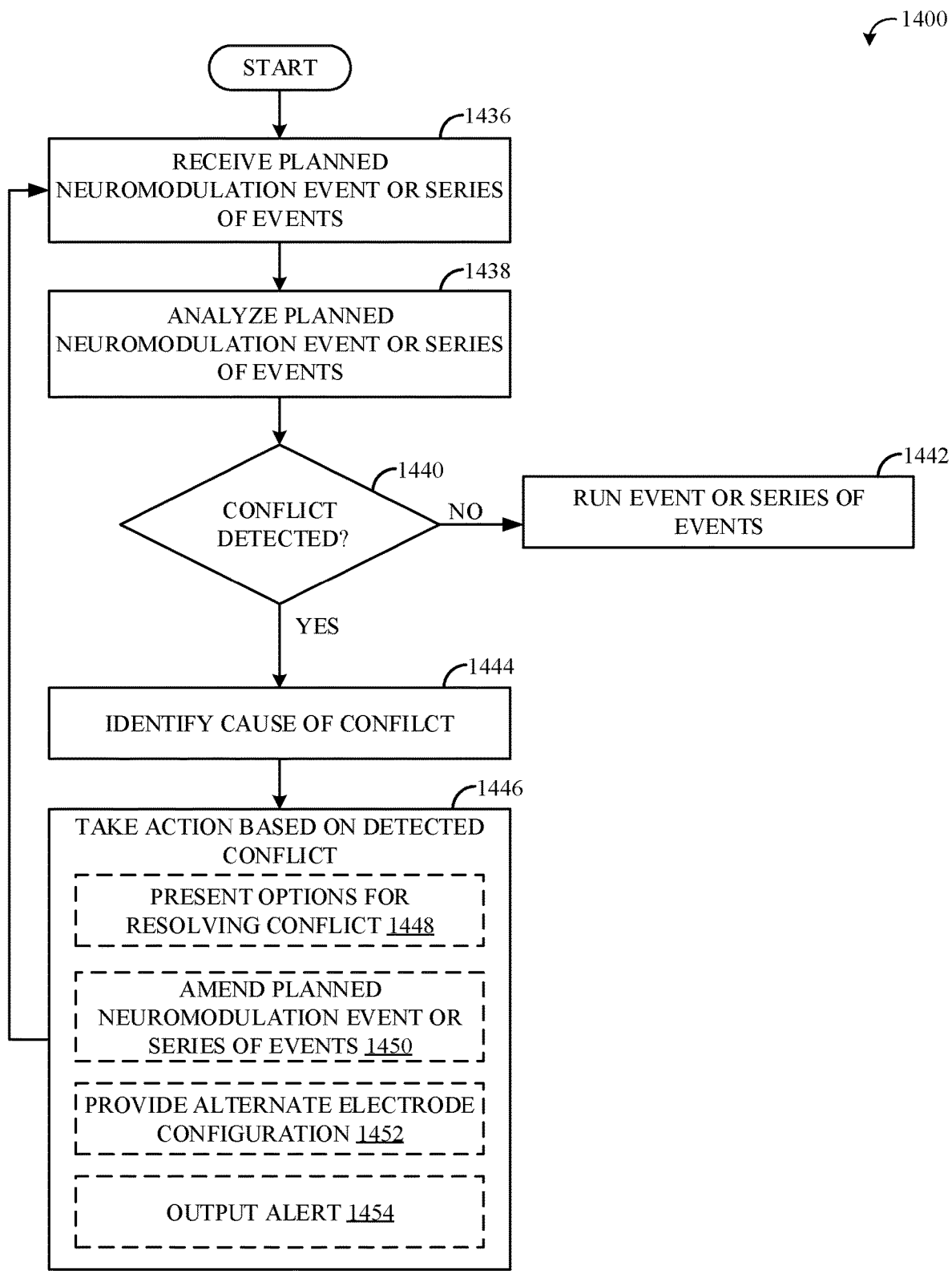
FIG. 14 depicts a flowchart illustrating an example method for identifying and correcting a conflict.

One further exemplary embodiment is shown in FIG. 13 when the user is informed about the systems limitations. In some embodiments, the output means 118 provide a note that the user must avoid placing too many stimulation blocks SB in parallel.

FIG. 14 shows a high-level flow chart 1400 for identifying and rectifying conflicts in a neuromodulation system according to an embodiment. In some embodiments, method 1400 provides the identification of a conflict in a planned neuromodulation event or series of events. Method 1400 is described with regard to systems, components, and methods of FIGS. 1 and 2, though it should be appreciated that method 1400 may be implemented with other systems, components, and methods without departing from the scope of the present disclosure. Method 1400 may be implemented as computer executable instruction in the memory 104, 204 executed by the processor 106, 206 of the device 102, 202.

Method 1400 may begin at 1436 receiving a planned neuromodulation event or series of events. Such an event or series of events may be selected from a preset menu or input manually into, for example, input module 212. The event or series of events can then be analyzed at 1438, for example by analyzing module 214 to identify any potential conflict. Such conflicts include, but are not limited to, one or more of incompatible electrode configuration(s) EC between stimulation blocks (SB), incompatible stimulation block (SB) timing properties (such as e.g. frequency, pulse width, pulse shape), incompatible stimulation block (SB) amplitude properties, and/or may relate to the safety or comfortability of the neurostimulation. If a conflict is not detected at 1440, the device 202 proceeds to run the neuromodulation event or series of events at 1442. If a conflict is detected at 1440, the cause of the conflict is identified at 1444. For example, the method may identify if the conflict is caused by one of neuromodulation safety, hardware capabilities, and/or software capabilities. Once the cause of the conflict is identified, one or more solutions for resolving the conflict may be taken at 1446. Such solutions may be taken individually or jointly in any order.

In some aspects, the options for resolving the conflict may be presented to the user at 1448, for example via a display via an output means such as output means 118. Possible options for resolving the conflict include, but are not limited to, preset configurations, suggestions for pulse interleaving, merging, amendment based on a Pseudo-Hamming Distance Criterion, and/or through the amendment of timing properties such as e.g. frequency, pulse width, pulse shape. In another example, taking an action may include amending the planned neuromodulation event or series of events at 1450. For example, the method may automatically amend the planned neuromodulation event or series of events at 1450 via a correction module, for example correction module 116. In another example, at 1452, the device may provide an alternate electrode configuration at 1452. Such an alternate electrode configuration may be presented as a series of presets as shown at FIG. 6, for example. In other aspects, the alternate electrode configuration may be a merger as shown in FIG. 5. In another example, if a conflict is detected at 1454, the device may output an alert. Such an alert may be auditory and/or visual as known to those of skill in the art. In some aspects, the alert may be presented on the display via output means 118. In some aspects different types of conflicts may generate different types of alerts. The planned neuromodulation event or series of events may be amended automatically, semi-automatically, or manually and then analyzed at 1436 for any further conflicts.

Those having skill in the art will appreciate that there are various logic implementations by which processes and/or systems described herein can be affected (e.g., hardware, software, and/or firmware), and that the preferred vehicle will vary with the context in which the processes are deployed. "Software" refers to logic that may be readily readapted to different purposes (e.g. read/write volatile or nonvolatile memory or media). "Firmware" refers to logic embodied as read-only memories and/or media. Hardware refers to logic embodied as analog and/or digital circuits. If an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

In a general sense, those skilled in the art will recognize that the various aspects described herein which can be implemented, individually and/or collectively, by a wide range of hardware, software, firmware, or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one Application specific integrated circuit, circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), circuitry forming a memory device (e.g., forms of random access memory), and/or circuits forming a communications device. (e.g., a modem, communications switch, or the like)

It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, are also regarded as included within the subject matter of the present disclosure.

The invention claimed is:

1. A neuromodulation system comprising:
at least one input module for inputting a planned neuromodulation event or a series of neuromodulation events of at least one stimulation block;
wherein the stimulation block comprises at least one electrode of an electrode array; and
wherein the stimulation block is activated to elicit or facilitate the movement of a patient; and
at least one analyzing module for analyzing a neuromodulation event or a series of neuromodulation events;
wherein the analyzing module and the input module are connected such that the input module is configured to forward the planned neuromodulation event or series of neuromodulation events to the analyzing module; and
wherein the analyzing module is configured to analyze the planned neuromodulation event or a series of neuromodulation events for one or more possible neuromodulation conflict(s).

2. The neuromodulation system according to claim 1, wherein the one or more possible neuromodulation conflict (s) is/are related to at least one of neuromodulation safety, hardware capabilities, software capabilities.

3. The neuromodulation system according to claim 2, wherein the conflict is incompatible electrode configuration between stimulation blocks, incompatible timing of stimulation blocks, or incompatible amplitude properties of the stimulation blocks.

4. The neurostimulation system according to claim 1, wherein the neuromodulation system further comprises at least one correction module which is configured to amend the planned neuromodulation event or series of neuromodulation events such that in case of detection of a neurostimulation conflict the neuromodulation event or series of neuromodulation events is/are amended such that the neuromodulation conflict is corrected.

5. The neurostimulation system according to claim 1, wherein the neuromodulation system further comprises output means, wherein the output means are connected to the analyzing module and is configured to provide at least partially a visual output of at least one of the analysis performed by an analysis module, the planned neuromodulation event or a series of neuromodulation events, the neuromodulation conflict(s), and the correction of the planned neuromodulation event or a series of neuromodulation events.

6. The neuromodulation system according to claim 1, wherein a conflict is an impossible electrode configuration.

7. The neuromodulation system according to claim 4, wherein the neuromodulation system is configured for a semi-automatic or automatic correction of the neuromodulation conflict.

8. The neuromodulation system according to claim 7, wherein the correction is selected from merging, interleaving pulses, amending VRAM available, amending computation time, replacing the planned neuromodulation event or series of neuromodulation events with one of an alternative preset, allowing some pulse overlap, or amending the timing properties.

9. The neuromodulation system according to claim 8, wherein the timing properties are frequency, pulse width, and pulse shape.

10. A method for performing neuromodulation, the method comprising at least the following steps:
analyzing a neuromodulation event or a series of neuromodulation events of at least one stimulation block;
wherein the stimulation block comprises at least one electrode of an electrode array; and
wherein the stimulation block is activated to elicit or facilitate movement of a patient;
wherein the analyzing includes the analysis whether the planned neuromodulation event or a series of neuromodulation events comprises one or more possible neuromodulation conflict(s) between at least two stimulation blocks.

11. The method of claim 10, wherein the one or more possible neuromodulation conflict(s) is/are related to at least one of neuromodulation safety, hardware capabilities, software capabilities.

12. The method of claim 11, wherein the conflict is incompatible electrode configuration between stimulation blocks, incompatible stimulation block timing, or incompatible stimulation block amplitude properties.

13. The method of claim 10, wherein the method further comprises the step of correcting the neuromodulation event or a series of neuromodulation events such that the one or more possible neuromodulation conflict(s) is/are avoided.

14. The method of claim 13, wherein the correction is automatic, semi-automatic, or manual.

15. The method according to claim 13, wherein the correction is selected from merging, interleaving pulses, amending VRAM available, amending computation time, replacing the planned neuromodulation event or series of neuromodulation events with one of an alternative preset, allowing some pulse overlap, or amending the timing properties.

16. The method according to claim 15, wherein the timing properties are frequency, pulse width, and pulse shape.

17. The method according to claim 16, wherein the pulse shape is amended by shortening biphasic pulses in a post-stimulation phase.

18. The method according to claim 15, wherein merging is selected when a frequency of the stimulation blocks in conflict is within 15 Hz.

19. The method according to claim 15, wherein merging is selected when an amplitude of the stimulation blocks in conflict is within 2 mA.

20. The method according to claim 10, wherein when a conflict is identified, the method computes a pulse distance matrix of the at least two stimulation blocks and when a timing between the at least two stimulation blocks is below a threshold, the amplitude of electrodes used by the stimulation blocks is lowered.

* * * * *